United States Patent [19]
Fleury et al.

[11] Patent Number: 6,030,630
[45] Date of Patent: *Feb. 29, 2000

[54] COSMETIC COMPOSITIONS FOR THE HAIR OR SKIN BASED ON SULFONE COPOLYESTERS WITH POLYORGANOSILOXANE UNITS

[75] Inventors: Etienne Fleury, Irigny; Jean-Marc Ricca, Paris, both of France

[73] Assignee: Rhodia Chimie, Courbevoie, France

[ * ] Notice: This patent is subject to a terminal disclaimer.

[21] Appl. No.: 09/101,076

[22] PCT Filed: Dec. 27, 1996

[86] PCT No.: PCT/FR96/02092

§ 371 Date: Jun. 29, 1998

§ 102(e) Date: Jun. 29, 1998

[87] PCT Pub. No.: WO97/24104

PCT Pub. Date: Jul. 10, 1997

[30] Foreign Application Priority Data

Dec. 29, 1995 [FR] France ................... 95 15713

[51] Int. Cl.$^7$ ............... A61K 7/00; A61K 7/42; A61K 7/06; A61K 31/74

[52] U.S. Cl. ................ 424/401; 424/59; 424/70.1; 424/70.12; 424/70.24; 424/70.7; 424/78.02; 424/78.03; 424/78.08

[58] Field of Search ............... 424/401, 70.1, 424/70.12, 70.24, 78.02, 70.7, 59, 78.03, 78.08

[56] References Cited

U.S. PATENT DOCUMENTS 5,283,296 2/1994 Canivenc et al. ............ 525/445
5,320,836 6/1994 Singleton ................... 424/71

*Primary Examiner*—Shelley A. Dodson
*Assistant Examiner*—Marina Lamm
*Attorney, Agent, or Firm*—John Daniel Wood; Jean-Louis Seugnet

[57] ABSTRACT

A cosmetic composition for the hair and/or skin comprising a water-dispersible sulfone copolyester with polyorganosiloxane units incorporating a plurality of recurrent sulfone polyester units and polyorganosiloxane units which have: a molecular mass number between 5000 and 45,000; a sulfur weight content of 0.5 to 6% compared with the said sulfone copolyesters with polyorganosiloxane units; and a silicium content of 0.05 to 20% by weight compared with the said sulfone copolyesters with polyorganosiloxane units.

18 Claims, No Drawings

COSMETIC COMPOSITIONS FOR THE HAIR OR SKIN BASED ON SULFONE COPOLYESTERS WITH POLYORGANOSILOXANE UNITS

This application is an application under 35 U.S.C. Section 371 of International Application Number PCT/FR96/02092, filed on Dec. 27, 1996.

The present invention relates to cosmetic compositions intended for use on the hair and/or the skin. They are based on sulfonated copolyesters containing polyorganosiloxane units; they can contain various other ingredients, in particular hair and/or skin conditioners. On account of their external application to the skin, these compositions can also be used to transport and/or deliver a certain number of cosmetic or pharmaceutical active products through the skin.

The expression cosmetic composition or formulation is understood to refer to any cosmetic product or preparation such as those described in Appendix I ("illustrative list by category of cosmetic products") of the European Directive No. 76/768/EEC of Jul. 27, 1976, known as the Cosmetic Directive.

The Applicant has found that certain sulfonated copolyesters containing polyorganosiloxane units are particularly suitable for use in cosmetic hair or skin compositions.

The subject of the present invention is a cosmetic hair and/or skin composition which comprises at least one water-dispersible sulfonated copolyester containing polyorganosiloxane units containing a plurality of repeating sulfonated polyester units and polyorganosiloxane units, said sulfonated copolyester containing polyorganosiloxane units having a number-average molecular mass from about 5000 to 45,000, preferably from about 8000 to 35,000, a weight content of sulfur from about 0.5 to 10%, preferably from about 1 to 8%, relative to said sulfonated copolyesters containing polyorganosiloxane units, and a silicon content from about 0.05 to 20%, preferably from about 0.1 to 10%, most particularly from about 0.1 to 5%, by weight relative to said sulfonated copolyesters containing polyorganosiloxane units.

Said water-dispersible sulfonated copolyester containing polyorganosiloxane units is most particularly chosen from those which can be obtained by polymerization (esterification and/or transesterification and polycondensation) of a monomer composition (M) based on:

at least one non-sulfonated aromatic dicarboxylic acid monomer (A), its anhydride or one of its diesters, at least one aliphatic or cycloaliphatic diol monomer (D), at least one sulfonated monomer (SM) chosen from sulfonated aromatic or sulfonated aliphatic dicarboxylic acids (SAM), their anhydrides or their diesters and sulfonated aliphatic or sulfonated aromatic diols (SDM), the relative amounts of the sulfonated or non-sulfonated monomers containing diacid, diester or anhydride functions, and of the sulfonated or non-sulfonated monomers containing diol functions corresponding to a ratio: number of OH functions in the monomer composition/number of COOH functions or equivalent functions in the monomer composition, from about 1.05 to 4, preferably from about 1.1 to 3.5, most particularly from about 1.8 to 3;

said polymerization operation being carried out in the presence of at least one polydiorganosiloxane reagent of formula (I)

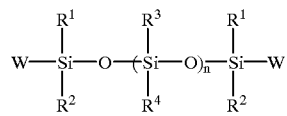

in which formula the symbols $R^1$, $R^2$, $R^3$ and $R^4$, which may be identical or different, represent linear or branched $C_1$–$C_{16}$, preferably $C_1$–$C_4$, alkyl radicals, $C_5$–$C_{15}$, preferably $C_6$–$C_8$, cycloalkyl radicals, phenyl radicals or alkylphenyl radicals with a $C_1$–$C_4$ alkyl part, W represents a group which can react with at least one of the monomers of the monomer composition (M) under the conditions of the polymerization operation, n is an integer or decimal number from about 5 to 15,000, preferably from about 30 to 300 and most particularly from about 50 to 200; the amounts of sulfonated monomer (SM) and of polyorganosiloxane, as well as the polymerization conditions, being such that said sulfonated copolyesters containing polyorganosiloxane units which are obtained have a number-average molecular mass from about 5000 to 45,000, preferably from about 8000 to 35,000, a weight content of sulfur from about 0.5 to 10%, preferably from about 1 to 8%, relative to said sulfonated copolyesters containing polyorganosiloxane units, and a silicon content from about 0.05 to 20%, preferably from about 0.1 to 10%, most particularly from about 0.1 to 5%, by weight relative to said sulfonated copolyesters containing polyorganosiloxane units.

The number-average molecular masses are measured by gel permeation chromatography, in dimethylacetamide containing $10^{-2}$ N LiBr, at 25° C. The results are expressed as polystyrene equivalents.

The non-sulfonated aromatic dicarboxylic acid monomers (A) are preferably chosen from terephthalic acid, isophthalic acid and 2,6-naphthalenedicarboxylic acid, their diesters or their anhydrides.

The non-sulfonated diacid monomer (A) preferably consists of about 0 to 100 mole %, preferably from about 50 to 100 mole %, most particularly from about 70 to 90 mole %, of terephthalic acid and/or isophthalic acid and/or 2,6-naphthalenedicarboxylic acid in the form of one of its (their) lower diesters (methyl, ethyl, propyl, isopropyl, butyl) and from about 100 to 0 mole %, preferably from about 50 to 0 mol %, most particularly from about 30 to 10 mole %, of isophthalic and/or 2,6-naphthalenedicarboxylic and/or terephthalic acid or anhydride.

Said non-sulfonated monomer (A) can consist most particularly of 50 to 90 mole %, most particularly from about 70 to 90 mol %, of terephthalic acid in the form of one of its (their) lower diesters (methyl, ethyl, propyl, isopropyl, butyl) and from about 50 to 10 mole %, preferably from about 30 to 10 mole %, of isophthalic acid or anhydride.

Along with these dicarboxylic acids (anhydrides or diesters), small amounts of other aromatic diacids such as orthophthalic acid, anthracenedicarboxylic acid, 1,8-naphthalene- dicarboxylic acid, 1,4-naphthalenedicarboxylic acid, biphenyldicarboxylic acid, or aliphatic diacids such as adipic acid, glutaric acid, succinic acid, trimethyladipic acid, pimelic acid, azelaic acid, sebacic acid, suberic acid, itaconic acid, maleic acid, etc., in the form of acid, anhydride or lower diesters (methyl, ethyl, propyl, isopropyl, butyl) can also be present.

Among the aliphatic or cycloaliphatic diol monomers (D), mention may be made of aliphatic oxyalkylene glycols containing from 1 to 100 oxyalkylene units, such as ethylene glycol, propylene glycol, diethylene glycol, dipropylene glycol and higher homologs thereof, 1,4-butanediol, 1,6-hexanediol, neopentyl glycol and alicyclic glycols such as cyclohexanediol, cyclohexanedimethanol, dicyclohexanediolpropane, etc.; the diol monomer (D) preferably used is monoethylene glycol and/or diethylene glycol.

The sulfonated monomer (SM) preferably consists of a sulfonated dicarboxylic acid (SAM) having at least one sulfonic acid group, preferably in the form of an alkali metal (in particular sodium), alkaline-earth metal, ammonium, quaternary ammonium, etc. sulfonate, and two acid functions attached to one or more aromatic rings, when they are aromatic dicarboxylic acids, or to the aliphatic chain, when they are aliphatic dicarboxylic acids.

Among the sulfonated monomers (SM), mention may be made of aromatic sulfonated dicarboxylic acids or anhydrides such as sulfoisophthalic, sulfoterephthalic or sulfoorthophthalic acids or anhydrides, 4-sulfo-2,7-naphthalenedicarboxylic acids or anhydrides, sulfo-4,4'-bis(hydroxycarbonyl)di-phenylsulfones, sulfo-diphenyl-dicarboxylic acids or anhydrides, sulfo-4,4'-bis(hydroxycarbonyl)diphenyl-methanes, sulfo-5-phenoxyisophthalic acids or anhydrides, or lower diesters thereof (methyl, ethyl, propyl, isopropyl, butyl) and aliphatic sulfonated dicarboxylic acids or anhydrides such as sulfosuccinic acids or anhydrides or lower diesters thereof (methyl, ethyl, propyl, isopropyl, butyl). The preferred sulfonated monomers are sulfoisophthalic and sulfosuccinic acids or anhydrides and the methyl diester thereof, and most particularly dimethyl sodio-5-oxysulfonylisophthalate.

Said sulfonated diacid monomer (SAM) can be used in an amount corresponding to an (SAM)/(A)+(SAM) molar ratio from about 5/100 to 40/100, preferably from about 7/100 to 15/100, most particularly from about 10/100 to 15/100.

The elementary species considered in the definition of a mole of monomer (A) or (SAM) is the COOH function in the case of diacids or the COOH function equivalent in the case of the anhydride or diesters.

The reactive polydiorganosiloxanes which can be used according to the invention are preferably those of formula (I) in which W represents an OH function or a group —A—Z, in which:

A represents a divalent hydrocarbon-based radical attached to the vicinal silicon atom via an Si—C or Si—O—C bond which can optionally contain a hetero atom taken from the group formed by O, Si, N and S.

Z represents a group which can react with at least one of the above monomers under the polymerization conditions.

Among the preferred radicals $R^1$, $R^2$, $R^3$ and $R^4$, which may be identical or different, mention may be made of the methyl, ethyl, n-propyl, isopropyl, n-butyl, isobutyl, n-pentyl, 2-ethylhexyl, n-decyl; cyclopentyl, cyclohexyl and phenyl radicals, the methyl radical being most particularly preferred.

Among the divalent radicals A, mention may be made of the following groups $C_1$–$C_5$, preferably $C_1$–$C_{12}$, alkylenes such as methylene, ethylene, 1,3-propylene, 1,4-butylene, alpha-methyl-1,3-propylene, 1,5-pentylene, hexamethylene, decamethylene, arylenes or polyarylenes such as phenylene, diphenylene or naphthylene, which are optionally substituted with one or more $C_1$–$C_4$ alkyl radicals, arylene-alkylenes consisting of a sequence of 1 or more arylene radicals [o, m or p-phenylene(s) optionally substituted with one or more $C_1$–$C_4$ alkyl radical(s)] and of one or more $C_1$–$C_{15}$ alkylene radical(s), alkylene-arylenes consisting of a $C_1$–$C_4$ alkylene radical and of one or more arylene radical(s), in particular phenylene(s), alkylenes, arylenes, polyarylenes or arylene-alkylenes, alkylene-arylenes as above, also containing 1 or more hetero atoms chosen from O, Si, N and S, such as polyoxyalkylene, phenylenoxyalkylene, etc.

Among the reactive groups Z, mentioned may be made of the groups OH, $NH_2$, NCO, COOH, COOX in which X represents a halogen atom (chlorine, bromine), or COOR in which R represents a linear or branched $C_1$–$C_8$ alkyl residue, preferably methyl.

As examples of reactive units W, mentioned may be made of

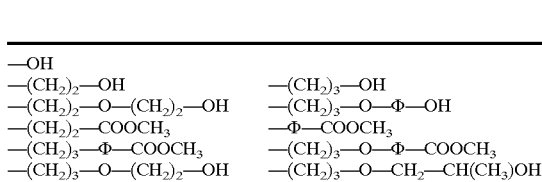

wherein Φ is phenyl

These reactive polyorganosiloxanes are products of known types; they can be prepared by the usual routes for the synthesis of difunctional polyorganosiloxanes; for example, they can be obtained by reacting a polyorganohydrogenosiloxane with a functional organic compound containing ethylenic unsaturation, in the presence of a platinum derivative, or alternatively by reaction of an organodialkyl-monochlorosilane containing a functional group with a polyorganosiloxane diol or one of the lower alkyl ethers thereof.

One way of preparing sulfonated copolyesters containing polysiloxane units of the type described above has already been mentioned in patent application EP-A-430,828.

The sulfonated copolyesters containing polysiloxane units described above can be obtained by the usual processes of esterification and/or transesterification and polycondensation, it being possible for the polyorganosiloxane to be introduced at any moment in the esterification and/or transesterification operation.

Thus, said sulfonated copolyesters containing polysiloxane units can be obtained by carrying out the following steps:

a step of esterification and/or transesterification between the sulfonated or non-sulfonated dicarboxylic acids, their diesters or anhydrides, and the sulfonated or non-sulfonated diols, the ratio: number of OH functions in the monomer composition/number of COOH functions or equivalent functions in the monomer composition being from about 1.05 to 4, preferably from about 1.1 to 3.5, most particularly from about 1.8 to 3, said polyorganosiloxane being introduced at any moment in this step, and a step of polycondensation.

The esterification and/or transesterification step can be carried out at a temperature greater than or equal to 130° C., preferably from about 140 to 220° C. and most particularly from about 180 to 220° C. This esterification and/or transesterification operation is preferably carried out in the presence of a metallic esterification or transesterification catalyst, in particular a metal carboxylate, such as manganese acetate, zinc acetate, cobalt acetate or calcium acetate, or an organic or inorganic titanate, such as butyl titanate, nitrilo-2,2',2"-triethyl titanate (or titanium aminotriethoxide) or calcium titanate. The preferred catalysts are organic titanates; they are used in amounts from about at least 0.001% by weight expressed as titanium, preferably from about 0.002% to 0.02% by weight of titanium relative to the weight of monomers present.

The duration of the esterification and/or transesterification operation is about 1 to 10 hours.

The reaction is carried out with formation of water and optionally an alcohol (methanol in the case of the use of at least one sulfonated or non-sulfonated dicarboxylic acid in the form of a methyl diester), which are removed from the reaction medium preferably by distillation at the same time as the excess diol.

The polycondensation operation is preferably carried out at a temperature from about 230 to 280° C., preferably from about 240 to 260° C., in another reactor brought to this temperature beforehand and gradually placed under vacuum to a pressure which depends on the desired molecular mass. The vacuum is then broken with nitrogen and the polymer is cast in a mold; after cooling, the polymer is ground.

The preferred sulfonated copolyesters containing polysiloxane units are those which can be obtained from isophthalic or terephthalic acid (A1) and/or from an isophthalic or terephthalic acid diester (A2), in an (A1)/(A2) molar ratio from about 0/100 to 100/0, preferably from about 0/100 to 50/50, most particularly from about 10/90 to 30/70, (A2) preferably being in the form of the methyl diester, from a sulfoisophthalic acid diester (SAM), preferably in the form of the methyl diester, in an (SAM)/(A1)+(A2)+(SAM) molar ratio from about 5/100 to 40/100, preferably from about 7/100 to 35/100, most particularly from about 10/100 to 15/100, from monoethylene glycol and/or from diethylene glycol (D), in a ratio: number of OH functions in (D)/number of COOH functions or equivalent functions in (A1)+(A2)+(SAM) from about 1.05 to 4, preferably from about 1.1 to 3.5, most particularly from about 1.8 to 3, from a polyorganosiloxane of formula (I) in an amount such that said sulfonated copolyester containing polyorganosiloxane units has a weight content of sulfur from about 0.5 to 10%, preferably from about 1 to 8%, relative to said sulfonated copolyesters containing polyorganosiloxane units, and a silicon content from about 0.05 to 20%, preferably from about 0.1 to 10%, most particularly from about 0.1 to 5%, by weight relative to said sulfonated copolyesters containing polyorganosiloxane units.

Most particularly advantageous sulfonated copolyesters containing polyorganosiloxane units are those which can be obtained from isophthalic acid (A1) and from a terephthalic acid diester (A2), in an (A1)/(A2) molar ratio from about 10/90 to 50/50, preferably from about 10/90 to 30/70 (A2) preferably being in the form of the methyl diester, from a sulfoisophthalic acid diester (SAM), preferably in the form of the methyl diester, in an (SAM)/(A1)+(A2)+(SAM) molar ratio from about 5/100 to 40/100, preferably from about 7/100 to 35/100, most particularly from about 10/100 to 15/100, from monoethylene glycol and/or from diethylene glycol (D), in a ratio: number of OH functions in (D)/number of COOH functions or equivalent functions in (A1)+(A2)+(SAM) from about 1.05 to 4, preferably from about 1.1 to 3.5, most particularly from about 1.8 to 3, from a polyorganosiloxane of formula (I) in an amount such that said sulfonated copolyester containing polyorganosiloxane units has a weight content of sulfur from about 0.5 to 10%, preferably from about 1 to 8%, relative to said sulfonated copolyesters containing polyorganosiloxane units, and a silicon content from about 0.05 to 20%, preferably from about 0.1 to 10%, most particularly from about 0.1 to 5%, by weight relative to said sulfonated copolyesters containing polyorganosiloxane units.

These preferred or particular sulfonated copolyesters containing polyorganosiloxane units can be prepared according to a preferred process by carrying out the following successive steps:

a transesterification step between, on the one hand, the terephthalic or isophthalic acid diester (A2) and the sulfoisophthalic acid diester (SAM) and, on the other hand, monoethylene glycol and/or diethylene glycol (D), the ratio: number of OH functions in (D)/number of COOH functions in (A2)+(SAM) being from about 1.05 to 4, preferably from about 1.1 to 3.5, most particularly from about 1.8 to 3, the diesters (A2) and (SAM) preferably being methyl diesters, an esterification step between isophthalic or terephthalic acid (A1) when it is present and, on the other hand, monoethylene glycol and/or diethylene glycol (D), the ratio: number of OH functions in (D)/number of COOH functions in (A1) being from about 1.05 to 4, preferably from about 1.1 to 3.5, most particularly from about 1.8 to 3, a polycondensation step, said polyorganosiloxane of formula (I) being introduced either in the transesterification step or in the esterification step, and preferably in the esterification step into the esterification medium.

The transesterification step is carried out in the presence of a metallic transesterification catalyst at a temperature greater than or equal to 130° C., preferably from about 140 to 220° C. and most particularly from about 180 to 220° C.; at this temperature, the methanol formed is removed from the reaction medium preferably by distillation. The duration of this operation is from about 1 to 4 hours, and generally from about 2 to 3 hours.

When more than 90% of the theoretical amount of methanol has been distilled off, the excess polyol is removed by raising the temperature of the reaction medium to 230° C.

The esterification operation is carried out by adding non-sulfonated aromatic dicarboxylic acid and the remaining fraction of diol (D), placed in suspension beforehand, to the reaction medium, at a temperature corresponding to that at the end of the transesterification; the introduction time is about 1 hour. This esterification operation is carried out at a temperature from about 230 to 280° C., preferably from about 250 to 260° C., in the presence of a catalyst of the same type as the transesterification catalyst; the reaction is carried out with removal of water, which is stripped from the reactor at the time as the excess diol.

The polyorganosiloxane of formula (I) is preferably introduced in the esterification step into the esterification medium.

The sulfonated copolyester containing polyorganosiloxane units thus obtained can be dispersed or dissolved in demineralized water until a solids content from about 3 to 30%, preferably from about 7 to 15% by weight is obtained;

this dispersion or solubilization operation is preferably carried out with stirring, at a temperature from about 60 to 80° C.

The amounts of sulfonated copolyesters containing polyorganosiloxane units which can be present in the cosmetic compositions of the invention can represent from 0.1 to 50%, preferably from about 0.1 to 5%, of the weight of said cosmetic compositions.

The sulfonated copolyester containing polyorganosiloxane units can be formulated as a large number of cosmetic hair and/or skin compositions, such as rinsing formulations, lotions, shampoos, conditioners, mousses, styling gels or any other formulation for styling or for making it easier to comb the hair, as well as hand or body lotions, cleansing milks, make-up-removing compositions, products for regulating skin moisturization, care creams, creams or milks for protection against sunlight and ultraviolet radiation, anti-acne preparations, local analgesics and mascaras; it can also be used as a constituent in solid, compact, homogeneous compositions such as toiletry bars and soaps.

Said sulfonated copolyester containing polyorganosiloxane units is present in the cosmetic composition in a vehicle, which is compatible with the hair and/or the skin, whose function is to convey said copolyester containing polyorganosiloxane units onto the hair and/or the skin when it is applied. This vehicle can represent from 0.5 to 99.5%, preferably from 5 to 99.5%, of the weight of the cosmetic composition.

The subject of the present invention is thus also a cosmetic composition comprising:
from 0.1 to 50%, preferably from 0.1 to 5%, by weight of the sulfonated copolyester containing polyorganosiloxane units described above, and
from 0.5 to 99.5%, preferably from 5 to 99.5%, by weight of a vehicle which is compatible with the hair and/or the skin.

The term "compatible with application to the hair and/or the skin" means here that the vehicle does not damage or exert negative effects on the appearance of the hair and/or the skin and does not cause any skin and/or eye and/or scalp irritation.

The vehicles which are compatible with the formulations described in this invention comprise, for example, those used in sprays, mousses, tonics, gels, shampoos or rinsing lotions. The choice of the appropriate vehicle will depend on the nature of the copolyester containing polyorganosiloxane units which is used, and on its destination, depending on whether the product formulated is intended to be left on the surface onto which it has been applied (for example sprays, mousses, tonic lotion or gels) or rinsed off after use (for example shampoo, conditioner, rinsing lotions).

The vehicles which can be used can thus be simple or complex, and they can include a large number of products usually used in cosmetic hair and/or skin compositions. The vehicle can be water optionally containing a solvent to dissolve or disperse the copolymer used, such as $C_1$–$C_6$ alcohols, and mixtures thereof, in particular methanol, ethanol, isopropanol and mixtures thereof. The vehicle can also contain a large variety of other compounds such as acetone, hydrocarbons (for instance isobutane, hexane, decene), halohydrocarbons (for instance freons), linalool, esters (for instance ethyl acetate, dibutyl phthalate) and volatile silicones (in particular siloxanes such as phenylpentamethylsiloxane, methoxypropylheptamethylcyclotetrasiloxane, chloropropylpentamethyldisiloxane, hydropropylpentamethyldisiloxane, octamethylcyclotetrasiloxane, decamethylcyclopentasiloxane, cyclodimethicone and dimethicone), and mixtures thereof. When the cosmetic compositions are in the form of sprays, tonic lotions, gels or mousses, the preferred solvents comprise water, ethanol, volatile silicone derivatives, and mixtures thereof. The solvents used in these mixtures can be miscible or immiscible with each other. The mousses and the aerosol sprays can also use any propellant capable of generating the products in the form of a mousse or fine, uniform spray. As examples, mention may be made of trichlorofluoromethane, dichlorodifluoromethane, difluoroethane, dimethyl ether, propane, n-butane or isobutane.

When the cosmetic compositions are used for a local application to the skin, the vehicles must have good esthetic properties, they must be compatible with the copolyesters containing polyorganosiloxane units and all the other components, and they must pose no toxicity or irritation problems.

These vehicles can take a wide variety of forms, for example emulsion, mousses, sprays, etc. For example, the vehicles in the form of emulsions include water-in-oil, oil-in-water and oil-in-water-in-silicone emulsions. These emulsions cover a wide viscosity range, for example from 100 to 200,000 mPa.s at 25° C. These emulsions can also be delivered in the form of sprays using either a device of mechanical pump type or in the form of an aerosol pressurized by the use of a propellent gas.

These vehicles can also be delivered in the form of a mousse.

Mention may be made, for example, of anhydrous liquid solvents, such as oils, alcohols and silicones, homogeneous aqueous mixtures such as aqueous-alcoholic mixtures, and rheologically modified versions of these two systems, for example when the viscosity of the system has been increased by the addition of gums, resins, polymers or salts).

The cosmetic compositions which form the subject of the invention can also contain other additives.

They can in particular contain fixing resins whose structure contains no silicone units.

These fixing resins are preferably dispersed or dissolved in the chosen vehicle with the silicone copolymer. These fixing resins can be of anionic, cationic, nonionic or amphoteric nature, or a mixture of these various natures. They are preferably of anionic or amphoteric nature.

These fixing resins are generally present in the cosmetic compositions at concentrations of between 0.5 and 10%, preferably between 1 and 5%. They are preferably chosen from the following resins: methyl acrylate/acrylamide copolymers, polyvinyl methyl ether/maleic anhydride copolymers, vinyl acetate/crotonic acid copolymers, octylacrylamide/methyl acrylate/butylaminoethyl methacrylate copolymers, polyvinylpyrrolidones, polyvinylpyrrolidone/methyl methacrylate copolymers, polyvinylpyrrolidone/vinyl acetate copolymers, polyvinyl alcohols, polyvinyl alcohol/crotonic acid copolymers, polyvinyl alcohol/maleic anhydride copolymers, hydroxypropylcelluloses, hydroxypropylguars, sodium polystyrene sulfonates, polyvinylpyrrolidone/ethyl methacrylate/methacrylic acid terpolymers, poly(methyl vinyl ether/maleic acid) monomethyl ethers, polyethylene glycol terephthalate/polyethylene glycol copolymers, polyethylene glycol terephthalate/polyethylene glycol/sodium polyisophthalate sulfonate copolymers, and mixtures thereof.

In addition, cationic resins can also be used. These cationic resins are partly or totally derived from cationic monomers such as, for example, dimethylaminoethyl methacrylate, quaternized dimethylaminoethyl methacrylate, diallyldimethyl-ammonium chloride or mixtures thereof. These cationic resins can also be based on natural water-soluble polymers such as, for example, cationic polysaccharides such as cationic guar, cationic cellulose or mixtures thereof.

The cosmetic compositions forming the subject of the invention can also contain polymer derivatives which exert a protective function.

These polymer derivatives can be present in amounts from about 0.01–10%, preferably about 0.1–5% and most particularly about 0.2–3% by weight, these being polymer derivatives such as cellulose derivatives such as cellulose hydroxy ethers, methylcellulose, ethylcellulose, hydroxypropylmethylcellulose, hydroxybutylmethylcellulose, polyvinyl esters grafted onto polyalkylene trunks, such as polyvinyl acetates grafted onto polyoxyethylene trunks (EP-A-219,048)

polyvinyl alcohols polyester copolymers based on ethylene terephthalate and/or propylene terephthalate and polyoxyethylene terephthalate units, with an ethylene terephthalate and/or propylene terephthalate (number of units)/polyoxyethylene terephthalate (number of units) molar ratio from about 1/10 to 10/1, preferably from about 1/1 to 9/1, the polyoxyethylene terephthalates having polyoxyethylene units with a molecular weight from about 300 to 5000, preferably from about 600 to 5000 (U.S. Pat. No. 3,959,230, U.S. Pat. No. 3,893,929, U.S. Pat. No. 4,116,896, U.S. Pat. No. 4,702,857, U.S. Pat. No. 4,770,666);

sulfonated polyester oligomers obtained by sulfonation of an oligomer derived from ethoxylated allyl alcohol, dimethyl terephthalate and 1,2-propylene diol, having from 1 to 4 sulfonated groups (U.S. Pat. No. 4,968,451), polyester copolymers based on propylene terephthalate and polyoxyethylene terephthalate units and ending with ethyl or methyl units (U.S. Pat. No. 4,711,730) or polyester oligomers ending with alkylpolyethoxy groups (U.S. Pat. No. 4,702,857) or sulfopolyethoxy (U.S. Pat. No. 4,721,580) or sulfoaroyl (U.S. Pat. No. 4,877,896) anionic groups, polyester-polyurethanes obtained by reaction of a polyester with a number-average molecular mass of 300–4000, obtained from adipic acid and/or from terephthalic acid and/or from sulfoisophthalic acid and from a diol with a mass of less than 300, with a prepolymer containing isocyanate end groups, obtained from a polyoxyethylene glycol with a molecular mass of 600–4000 and from a diisocyanate (FR-A-2,334, 698), ethoxylated monoamines or polyamines, ethoxylated amine polymers (U.S. Pat. No. 4,597,898, EP-A-11, 984), sulfonated polyester oligomers obtained by condensation of isophthalic acid, dimethyl sulfosuccinate and diethylene glycol (FR-A-2,236,926).

The performance of the cosmetic compositions forming the subject of the invention can also be improved by using plasticizers. The plasticizer may constitute between 0.1 and 20% of the formulation, preferably from 1 to 15%. Among the plasticizers which are particularly useful, mention may be made of adipates, phthalates, isophthalates, azelates, stearates, silicone copolyols, glycols, castor oil or mixtures thereof.

These cosmetic compositions can also contain surfactants which serve to disperse, emulsify, dissolve or stabilize various compounds used for their emollient or wetting properties. The surfactants are used in these compositions in concentrations ranging from 0.05 to 50% by weight of the preparation. Anionic, nonionic, cationic, zwitterionic or amphoteric surfactants or mixtures of these surfactants are thus found.

Among these surfactants are anionic surfactants such as alkyl ester sulfonates of formula R—CH(SO$_3$M)—COOR', where R represents a $C_8$–$C_{20}$, preferably $C_{10}$–$C_{16}$, alkyl radical, R' represents a $C_1$–$C_6$, preferably $C_1$–$C_3$, alkyl radical, and M represents an alkali-metal (sodium, potassium or lithium) cation, a substituted or unsubstituted ammonium cation (methyl-, dimethyl-, trimethyl-, tetramethylammonium, dimethylpiperidinium etc.) or an alkanolamine derivative (monoethanolamine, diethanolamine, triethanolamine, etc.). Mention may be made most particularly of methyl ester sulfonates in which the radical R is $C_{114}$–$C_{16}$;

alkyl sulfates of formula ROSO$_3$M, where R represents a $C_{10}$–$C_{24}$, preferably $C_{12}$–$C_{20}$ and most particularly $C_{12}$–$C_{18}$, alkyl or hydroxyalkyl radical, M representing a hydrogen atom or a cation of the same definition as above, as well as the ethoxylated (EO) and/or propoxylated (PO) derivatives thereof, having on average from 0.5 to 6, preferably from 0.5 to 3, EO and/or PO units;

alkylamide sulfates of formula RCONHR'OSO$_3$M where R represents a $C_2$–$C_{22}$, preferably $C_6$–$C_{20}$, alkyl radical, R' represents a $C_2$–$C_3$ alkyl radical, M representing a hydrogen atom or a cation of the same definition as above, as well as the ethoxylated (EO) and/or propoxylated (PO) derivatives thereof, having on average from 0.5 to 60 EO and/or PO units;

saturated or unsaturated $C_8$–$C_{24}$, preferably $C_{14}$–$C_{20}$, fatty acid salts, $C_9$–$C_{20}$ alkylbenzene sulfonates, primary or secondary $C_8$–$C_{22}$ alkyl sulfonates, alkylglyceryl sulfonates, the sulfonated polycarboxylic acids described in GB-A-1,082,179, paraffin sulfonates, N-acyl N-alkyl taurates, alkyl phosphates, alkyl isethionates, alkyl succinamates, alkyl sulfosuccinates, sulfosuccinate monoesters or diesters, N-acyl sarcosinates, alkylglycoside sulfates, polyethoxycarboxylates, the cation being an alkali metal (sodium, potassium, lithium), a substituted or unsubstituted ammonium residue (methyl-, dimethyl-, trimethyl-, tetramethylammonium, dimethylpiperidinium, etc.) or an alkanolamine derivative (monoethanolamine, diethanolamine, triethanolamine, etc.);

nonionic surfactants such as polyoxyalkylenated (polyethoxyethylenated, polyoxypropylenated, polyoxybutylenated) alkylphenols in which the alkyl substituent is $C_6$–$C_{12}$ and contains from 5 to 25 oxyalkylene units; by way of example, mention may be made of Triton X-45, X-114, X-100 or X-102 sold by Rohm & Haas Cy.;

glucosamides, glucamides;

glycerolamides derived from N-alkylamines (U.S. Pat. No. 5,223,179 and FR-A-1,585,966)

polyoxyalkylenated $C_8$–$C_{22}$ aliphatic alcohols containing from 1 to 25 oxyalkylene (oxyethylene, oxypropylene) units; by way of example, mention may be made of Tergitol 15-S-9, Tergitol 24-L-6 NMW sold by Union Carbide Corp., Neodol 45-9, Neodol 23-65, Neodol 45-7, Neodol 45-4 sold by Shell Chemical Cy., and Kyro EOB sold by The Procter & Gamble Co.

products resulting from the condensation of ethylene oxide with a hydrophobic compound resulting from the condensation of propylene oxide with propylene glycol, such as the Pluronic products sold by BASF;

amine oxides such as $C_{10}$–$C_8$ alkyl dimethylamine oxides, $C_8$–$C_{22}$ alkoxy ethyldihydroxyethylamine oxides;

the alkylpolyglycosides described in U.S. Pat. No. 4,565,647 and the polyoxyalkylenated derivatives thereof;

$C_8$–$C_{20}$ fatty acid amides ethoxylated fatty acids ethoxylated amides, amines, and amino amides cationic surfactants such as alkyldimethylammonium halides, amphoteric and zwitterionic surfactants such as alkyl amphoacetates and diacetates, alkylbetaines, alkylamidopropylbetaines, alkyltrimethylsulfobetaines, condensation products of fatty acids and of protein hydrolyzates, alkyl amphopropionates or -dipropionates, alkylsultaines, amphoteric derivatives of alkylpolyamines, such as Amphionic XL® sold by Rhône-Poulenc, Ampholac 7T/X® and Ampholac 7C/X® sold by Berol Nobel are used to reduce the irritation caused by the other surfactants, mainly the anionic surfactants.

In order further to reduce the skin irritation or attack, water-soluble or water-dispersible polymers can also be added, such as collagen or certain non-allergenic derivatives of animal or plant proteins (for example wheat protein hydrolyzates), natural hydrocolloids (guar gum, carob gum, tara gum, etc.) or obtained from fermentation processes, such as xanthan gum and derivatives of these polycarbohydrates, such as modified celluloses (for example hydroxyethylcellulose, carboxymethylcellulose, cationic celluloses—the Polymer JR products sold by the company Union Carbide), guar derivatives or carob derivatives, such as their cationic derivatives (Jaguar C13S, Jaguar C162 sold by Rhône-Poulenc) or nonionic derivatives (for example hydroxypropylguar), anionic derivatives (carboxymethylguar) or nonionic/anionic mixed derivatives such as carboxyhydroxypropylguars or nonionic/cationic mixed derivatives. Synthetic polymers can also be added, alternatively or in combination, such as synthetic cationic polyacrylates or polymers, known under the generic CTFA name of "Polyquaternium", for example the polymers Mirapol A15 or Mirapol 550 from the company Rhône-Poulenc.

It is also advantageously possible to add metal-sequestering agents to these compositions, more particularly calcium-sequestering agents such as citrate ions, or emollients such as silicones or oils or fatty substances used for this purpose in the cosmetics industry (mineral oils, fatty acid esters, triglycerides, silicones, etc.).

One or more fragrances, dyes and/or opacifiers such as pigments (titanium oxide particles) are generally added to these ingredients. Bactericides or fungicides can also be incorporated into the composition in order to improve the disinfection of the skin, for example such as triclosan.

Among the wetting agents, mention may be made of glycerol, sorbitol, urea, collagen, gelatin, Aloe vera, hyaluronic acid, etc.

The emollients are generally chosen from alkylmonoglycerides, alkyldiglycerides, triglycerides such as oils extracted from plants and vegetables (palm oil, coconut oil, cottonseed oil, soybean oil, sunflower oil, olive oil, grapeseed oil, sesame oil, groundnut oil, castor oil, etc.) or oils of animal origin (tallow, fish oils, etc.), derivatives of these oils such as hydrogenated oils, lanolin derivatives, mineral oils or paraffin oils, perhydrosqualane, squalene, diols such as 1,2-propanediol, 1,3-butanediol, cetyl alcohol, stearyl alcohol, oleyl alcohol, polyethylene glycols or polypropylene glycols, fatty esters such as isopropyl palmitate, 2-ethylhexyl cocoate, myristyl myristate, lactic acid esters, stearic acid, behenic acid, isostearic acid, silicone oils including cyclic polydimethylsiloxanes, $\alpha,\omega$-hydroxylated polydimethylsiloxanes, $\alpha,\omega$-trimethylsilylated polydimethylsiloxanes, polyorganosiloxanes such as polyalkylmethylsiloxanes, polymethylphenylsiloxanes, polydiphenylsiloxanes, aminosilicone derivatives, silicone waxes, copolyether silicones (such as the oil Silbione 70646 sold by the company Rhône-Poulenc or DC 190 sold by Dow Corning) or mixed silicone derivatives including various types of derivatization (such as polyalkylmethylsiloxane-silicone copolyether mixed copolymers).

Inorganic particles or powders such as calcium carbonate, inorganic oxides in powder form or in colloidal form (particles of less than or about one micrometer in size, occasionally a few tens of nanometers), such as titanium dioxide, silica, aluminium salts generally used as antiperspirants, kaolin, talc, clays and derivatives thereof, etc., can be added, in combination, to these compounds.

Preserving agents such as the methyl, ethyl, propyl and butyl esters of p-hydroxybenzoic acid, sodium benzoate, Germaben (trade mark) or any chemical agent which prevents bacterial or mould proliferation and which is used conventionally in cosmetic compositions are generally introduced into these compositions to a level of 0.01 to 3% by weight. The amount of these products is generally adjusted in order to prevent any bacterial, mould or yeast proliferation in the cosmetic compositions.

As an alternative to these chemical agents, it is occasionally possible to use water-activity modifiers which increase the osmotic pressure greatly, such as carbohydrates or salts.

In order to protect the skin and/or the hair against attack by sunlight and UV rays, sunscreens can be added to these formulations, the sunscreens being either chemical compounds which absorb UV radiation strongly, such as compounds authorized in European Directive No. 76/768/EEC, its appendices and the subsequent modifications to this Directive, or titanium dioxide or cerium oxides in powder form or in the form of colloidal particles. These powders can optionally be surface-treated in order to increase the efficacy of their anti-UV action or in order to facilitate their incorporation into the cosmetic formulations or in order to inhibit the surface photoreactivity.

Fragrances, dyes or pigments can be added in order to make the composition more pleasant for consumers to use.

Finally, the composition can also contain viscosity-modifying or gelling polymers, such as the Carbopol crosslinked polyacrylates sold by Goodrich, cellulose derivatives such as hydroxypropylcellulose, carboxymethylcellulose, guars and derivatives thereof, carob, tara gum or cassia gum, xanthan gum, alginates, carrageenans, chitin derivatives such as chitosan, etc. used alone or in combination, or the same compounds, generally in the form of water-soluble polymers modified with hydrophobic groups linked covalently to the polymer skeleton, as described in patent WO 92/16187 and/or water, in order to bring the total for the constituents of the formulation to 100%.

The cosmetic compositions forming the subject of the invention can also contain polymeric dispersing agents in an amount from about 0.1–7% by weight, in order to control the calcium and magnesium hardness, these being agents such as water-soluble salts of polycarboxylic acids with a molecular mass from about 2000 to 100,000, obtained by polymerization or copolymerization of ethylenically unsaturated carboxylic acids such as acrylic acid, maleic acid or anhydride, fumaric acid, itaconic acid, aconitic acid, mesaconic acid, citraconic acid or methylenemalonic acid, and most particularly polyacrylates with a molecular mass from about 2000 to 10,000 (U.S. Pat. No. 3,308,067), and copolymers of acrylic acid and of maleic anhydride with a molecular mass from about 5000 to 75,000 (EP-A-66,915);

polyethylene glycols with a molecular mass from about 1000 to 50,000.

The cosmetic compositions forming the subject of the invention can also contain any type of product intended to temporarily modify the external coloration of a body surface. As examples, mention may be made of dye products for the hair, make-up products such as lipsticks, nail varnishes or eyebrow and eyelash products.

Among the dyes which can be used as constituents of the cosmetic compositions forming the subject of the invention, mention may be made of the products described in Appendix IV ("list of colouring agents allowed for use in cosmetic products") of European Directive No. 76/768/EEC of Jul. 27, 1976, known as the Cosmetic Directive.

The compositions resulting from this invention can also be used in toiletry bar formulations known as soaps.

The standard toiletry bar compositions generally comprise fatty acid salts used in combination with surfactants of the invention and optionally surfactants other than the fatty acid salts or the fatty acids themselves. These compositions can even contain no fatty acid or fatty acid salt and, in this case, their formulations are based on other surfactants such as, for example, sodium ($C_8$–$C_{22}$) alkyl isethionates or sodium ($C_8$–$C_{22}$) alkyl sulfates.

Various useful constituents for moisturizing the skin can also be added to these compositions, such as certain carbohydrates (glycerol or sorbitol for example), polyethylene glycols or polypropylene glycol, alkoxylated sugar derivatives or derivatives thereof (for example methylglucose), water-soluble or water-dispersible polymers such as collagen or certain non-allergenic animal or plant protein derivatives (for example wheat protein hydrolyzates), natural hydrocolloids (guar gum, carob gum, tara gum, etc.) or obtained from fermentation processes, such as xanthan gum and derivatives of these polycarbohydrates, such as modified celluloses (for example hydroxyethylcellulose, carboxymethylcellulose, cationic celluloses—such as the Polymer JR® products sold by the company Union Carbide), guar derivatives or carob derivatives, such as their cationic derivatives (Jaguar C13S®, Jaguar C162® sold by Rhône-Poulenc) or nonionic derivatives (for example hydroxypropylguar), anionic derivatives (carboxymethylguar) or nonionic/anionic mixed derivatives such as carboxyhydroxypropylguars or nonionic/cationic mixed derivatives. Synthetic polymers can also be added, alternatively or in combination, such as synthetic cationic polyacrylates or polymers, known under the generic CTFA name of "Polyquaternium", for example the polymers Mirapol A15® or Mirapol 550® from the company Rhône-Poulenc.

It is also advantageously possible to add metal-sequestering agents to these compositions, more particularly calcium-sequestering agents such as citrate ions, or emollients such as silicones or oils or fatty substances used for this purpose in the cosmetics industry (mineral oils, fatty acid esters, triglycerides, silicones, etc.).

One or more fragrances, dyes and/or opacifiers such as pigments (titanium oxide particles) are generally added to these ingredients. Bactericides or fungicides can also be incorporated into the composition in order to improve the disinfection of the skin.

In a toiletry bar whose formulation consists mainly of soaps of monocarboxylic fatty acids (sodium, potassium, mono-, di- or triethanolammonium salts), the contents of fatty acid soaps are generally more than 25% by weight of the formulation, generally from 30 to 95% by weight.

In a toiletry bar whose formulation is based on main constituents other than fatty acid soaps, from 0 to 50% by weight, preferably from 1 to 40% by weight of these fatty acid soaps are found in the formulation.

These toiletry bar compositions can also contain from 0 to 95%, preferably from 0 to 60% of surfactants other than soaps, in particular $C_8$–$C_{22}$ alkyl or alkenyl isethionates, as well as the compositions resulting from this invention, alkylampho-propionates or -dipropionates.

From 1 to 15% of free $C_8$–$C_{22}$ fatty acids can also be introduced into the soap compositions as super-fatting agents or in order to modify the appearance and creamy nature of the mousse during washing.

Waxes such as paraffin waxes, natural waxes such as beeswax or ozokerite or silicone waxes can also be found in these compositions. These waxes are advantageously used to improve the appearance, the quality, the processability and the conservation on storage of the toiletry bars.

The examples which follow are given by way of illustration.

EXAMPLE 1

The following are introduced, while cold, into a 7.5-liter stainless-steel reactor fitted with an anchor-shaped stirrer, a jacket for circulating a heat-exchange liquid, and a distillation column controlled by an electrovalve:

2363 g (12.17 mol) of dimethyl terephthalate (DMT)

590 g (1.99 mol) of dimethyl 5-sulfooxysulfonylisophthalate (DSIP)

2464 g (39.7 mol) of ethylene glycol (EG)

1.34 g of butyl orthotitanate (TBOT) as polycondensation and exchange catalyst.

The diol/diester molar ratio MR1 is 2.80.

The stirrer is switched on and the contents of the reactor are then brought rapidly to 182° C., at which temperature the methanol begins to distil off. The temperature of the reaction mixture is then maintained at 220–230° C. for about 120 minutes in order to distil off all of the methanol and some of the excess ethylene glycol. When the reaction mass reaches 230° C., the isophthalic acid/ethylene glycol suspension below is introduced over a period of 1 hour:

497 g (2.99 mol) of isophthalic acid (IA)

497 g (8.00 mol) of ethylene glycol (EG).

The diol/diacid molar ratio MR2 is 2.67.

During the introduction, the temperature of the reaction mass does not fall below 227° C. and does not exceed 233° C.

As soon as the introduction of the above suspension is complete, 70 g (i.e. 2% by weight relative to the theoretical amount of non-silicone polyester formed by using the above diesters, diacids and diols) of the oligomer (S1) consisting of polydimethylsiloxane methyl α,ω-bispropyloxybenzoate with a molecular weight from about 6400, are also introduced into the reactor, the methyl propyloxybenzoate units α- and ω-linked to the silicon atoms having the formula

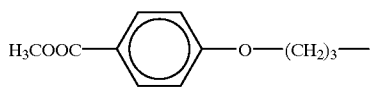

The reaction mass is then maintained at 230° C. to 250° C. for 1 hour. During this period, a water/ethylene glycol/methanol mixture is distilled off. At 250° C., the reaction mass is transferred into an autoclave preheated to 250° C. The pressure is then reduced from 1013 millibar to 1 millibar over 60 minutes and the polycondensation is continued for about 40 to 45 minutes, still at 250° C. and with a strong vacuum which ranges between 0.5 and 1 millibar.

The polymer is then poured out and cooled.

The following analyses are carried out:

1. Evaluation of the molar mass by gel permeation chromatography (GPC) in dimethylacetamide/LiCl at 20° C. The values are given as polystyrene equivalents.
2. Evaluation of the silicon content in the polymer by dry-route mineralization in the presence of alkaline carbonates and analysis by inductively-coupled plasma-generated atomic emission spectrometry of the alkaline silicate solution obtained above.
3. Turbidity in aqueous dispersion containing 25% by weight of solids, measured using a Ratio/XR turbidimeter ("Hach" 43900 model).
4. Measurement of the sulfur content.

The characteristics of the sulfonated copolyester containing polyorganosiloxane units prepared are given in Table 1.

EXAMPLE 2

Example 1 is repeated following the same procedure, but replacing the oligomer (S1) by the same amount of oligomer (S2) consisting of α,ω-bis(hydroxy)-polydimethylsiloxane with a molecular weight from about 11,000.

The characteristics of the sulfonated copolyester containing polyorganosiloxane units prepared are given in Table 1.

EXAMPLE 3

Example 2 is repeated, introducing 140 g of the oligomer S2 (4%) instead of 70 g.

The characteristics of the sulfonated copolyester containing polyorganosiloxane units prepared are given in Table 1.

EXAMPLE 4

Example 2 is repeated, introducing 280 g of the oligomer S2 (8%) instead of 70 g.

The characteristics of the sulfonated copolyester containing polyorganosiloxane units prepared are given in Table 1.

EXAMPLE 5

Example 1 is repeated following the same procedure, but replacing the 2% of oligomer (S1) by 4% (140 g) of oligomer (S3) consisting of (α,ω-bis(hydroxypropyl) polydimethylsiloxane with a molecular weight in the region of 6400, the hydroxypropyl units α- and ω-linked to the silicon atoms having the formula —$(CH_2)_3$—OH.

The characteristics of the sulfonated copolyester containing polyorganosiloxane units prepared are given in Table 1.

TABLE 1

| Example | Oligomer | % oligomer introduced | Si assayed | % Si | Mn | Mw | Turbidity (NTU) |
|---|---|---|---|---|---|---|---|
| 1 | S1 | 2 | 0.47 | 1.63 | | | 172 |
| 2 | S2 | 2 | 0.49 | 1.63 | | | 450 |
| 3 | S2 | 4 | 1.00 | 1.66 | 29,600 | 55,800 | 810 |
| 4 | S2 | 8 | 2.32 | 1.7 | 26,000 | 53,600 | >2000 |
| 5 | S3 | 4 | 1.15 | 1.66 | 28,800 | 53,330 | 760 |

EXAMPLE 6

Composition of a Hair Fixing Spray

| Component | % by weight |
|---|---|
| Product of one of Examples 1–5 | 3 |
| Ethanol | 75 |
| Fragrance | 0.1 |
| Propellent gas | qs 100 |

EXAMPLE 7

Structuring Shampoo

| Component | % by weight |
|---|---|
| Structuring agent | |
| Product of one of Examples 1–5 | 2 |
| Octamethylcyclotetrasiloxane | 2 |
| Premix | |
| Silicone gum | 0.5 |
| Dimethicone | 0.5 |
| Main mix | |
| Ammonium lauryl sulfate | 11 |
| Cocoamphodiacetate | 2 |
| Ethylene glycol distearate | 1 |
| Xanthan gum | 1 |
| Preserving agent | 1.2 |
| Citric acid qs pH 6.5 | qs pH 6.5 |
| Distilled water | qs 100 |

The structuring agent and the premix are prepared separately in a conventional manner. The main mix is prepared by first dissolving the xanthan gum in the water. Next, the other compounds are added and the main mix is heated with stirring at 80° C. for 30 minutes. The structuring agent and the premix are then added sequentially, after which the residual mixture is left to cool to room temperature with stirring.

EXAMPLE 8

Shampoo

| Component | % by weight |
|---|---|
| Ammonium lauryl sulfate | 7 |
| Ammonium lauryl ether sulfate | 5 |
| Cocoamphodiacetate | 4 |
| Product of one of Examples 1–5 | 1 |
| Hydroxypropylguar | 1 |

EXAMPLE 9
Conditioning Shampoo

| Component | % by weight |
|---|---|
| Structuring agent | |
| Product of one of Examples 1–5 | 1 |
| Phenylpentamethyldisiloxane | 4 |
| Silicone premix | |
| Silicone gum | 0.3 |
| Octamethyltetrasiloxane | 1.7 |
| Main mix | |
| Cetyl/stearyl alcohols | 1.7 |
| Hydroxypropyltrimoniumguar chloride | 0.85 |
| Hydroxypropylguar | 0.5 |
| Ceteareth-20 | 0.35 |
| Fragrance | 0.2 |
| Dimethicone copolyol | 0.2 |
| Preserving agent | 0.04 |
| Distilled water | qs 100 |

EXAMPLE 10
Styling Gel

| Component | % by weight |
|---|---|
| Product of one of Examples 1–5 | 2 |
| Hydroxypropylguar | 0 |
| Triethanolamine | 1 |
| Dye | 0.05 |
| Fragrance | 0.1 |
| Laureth-23 | 0.1 |
| Distilled water | qs 100 |

EXAMPLE 11
Conditioning Shower Gel

| Component | CTFA name | % w/w |
|---|---|---|
| Distilled water | Water | qs 100 |
| Empicol ESB | Sodium laureth-2 sulfate | 25.0 |
| Miranol Ultra C32 | Sodium cocoamphoacetate | 10.0 |
| Geropon TC42 | Sodium methyl cocoyl taurate | 12.0 |
| Product of one of Examples 1–5 | | 0.3 |
| Glycerol | Glycerol | 1.0 |
| Silbione 71834 | Diphenyldimethicone emulsion | 2.00 |
| Mirasheen 202 | | 8.0 |
| Germaben II | | 0.20 |
| Fragrance (Parfex 49902) | | 0.20 |
| Citric acid | Citric acid | qs pH 6.5 |
| NaCl | Sodium chloride | qs* | qs*: qs to obtain a viscosity of 4000 mPa.s at 25° C.

EXAMPLE 12
Styling Mousse

| Component | % w/w |
|---|---|
| Water | qs 100 |
| Product of one of Examples 1–5 | 3 |
| Cocoamphodiacetate | 0.5 |
| Sodium methyl oleyl taurate | 2 |
| DMDM hydantoin | 0.8 |
| Ethoxylated isostearyl alcohol | 0.1 |
| Fragrance | 0.1 |
| Propellent gas | 7 |
| Disodium EDTA | 0.2 |

EXAMPLE 13
Anti-acne Composition

| Component | % w/w |
|---|---|
| Water | qs 100 |
| Salicylic acid | 2 |
| Product of one of Examples 1–5 | 2 |
| Ethanol | 40 |

What is claimed is:

1. A cosmetic hair or skin composition comprising at least one water-dispersible sulfonated copolyester containing polyorganosiloxane units having a plurality of repeating sulfonated polyester units and polyorganosiloxane units, said sulfonated copolyester containing polyorganosiloxane units having:

a number-average molecular mass from about 5000 to 45,000, a weight content of sulfur from about 0.5 to 10%, relative to said sulfonated copolyesters containing polyorganosiloxane units, and a silicon content from about 0.05 to 20% by weight relative to said sulfonated copolyesters containing polyorganosiloxane units;

said composition comprising:

from about 0.1 to 50% of its weight of said sulfonated copolyester containing said polyorganosiloxane units, and from about 0.5 to 99.5% of its weight of a vehicle compatible with the hair or the skin.

2. A cosmetic hair or skin composition according to claim 1, wherein said sulfonated copolyester has:

a number-average molecular mass from about 8000 to 35,000, a weight content of sulfur from about 1 to 8%, relative to said sulfonated copolyesters containing polyorganosiloxane units, and a silicon content from about 0.1 to 5%, by weight relative to said sulfonated copolyesters containing polyorganosiloxane units.

3. A cosmetic composition as claimed in claim 1, wherein said water-dispersible sulfonated copolyester containing polyorganosiloxane units is a water-dispersible sulfonated copolyester containing polyorganosiloxane units which is obtained by polymerization of a monomer composition comprising:

at least one non-sulfonated aromatic dicarboxylic acid monomer, an anhydride thereof, or a diester thereof, at least one aliphatic or cycloaliphatic diol monomer, at least one sulfonated monomer selected from the group consisting of sulfonated aromatic dicarboxylic acids, the anhydrides of sulfonated aromatic dicarboxylic acids, the diesters of sulfonated aromatic dicarboxylic acids, sulfonated aliphatic dicarboxylic acids, the anhydrides of sulfonated aliphatic dicarboxylic acids, the diesters of sulfonated aliphatic dicarboxylic acids, sulfonated aliphatic diols, and sulfonated aromatic diols, the relative amounts of the sulfonated or non-sulfonated monomers containing diacid, diester or anhydride functions, and of the sulfonated or non-sulfonated monomers containing diol functions corresponding to a ratio: number of OH functions in the monomer composition/number of COOH functions or equivalent functions in the monomer composition, from about 1.05 to 4; said polymerization operation being carried out in the presence of at least one polydiorganosiloxane reagent of formula (I)

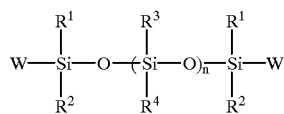

wherein:

the symbols $R^1$, $R^2$, $R^3$ and $R^4$, which may be identical or different, represent linear or branched $C_1$–$C_{16}$, alkyl radicals, $C_5$–$C_{15}$, cycloalkyl radicals, phenyl radicals or alkylphenyl radicals with a $C_1$–$C_4$ alkyl part, W represents a group which can react with at least one of the monomers of the monomer composition, n is an integer or decimal number from about 5 to 15,000;

the amounts of sulfonated monomer and of polyorganosiloxane, as well as the polymerization conditions, being such that said sulfonated copolyesters containing polyorganosiloxane units which are obtained have:

a number-average molecular mass from about 5000 to 45,000, a weight content of sulfur from about 0.5 to 10%, relative to said sulfonated copolyesters containing polyorganosiloxane units, and a silicon content from about 0.05 to 20%, by weight relative to said sulfonated copolyesters containing polyorganosiloxane units.

4. A cosmetic composition as claimed in claim 3, wherein the non-sulfonated diacid monomer consists of about 0 to 100% by mole, of a lower dialkyl ester of one or more members selected from the group consisting of terephthalic acid, isophthalic acid, and 2,6-naphthalenedicarboxylic acid, said alkyl being methyl, ethyl, propyl, isopropyl, or butyl, and from about 0 to 100% by mole, of an acid, or anhydride thereof, of one or more members selected from the group consisting of isophthalic acid, 2,6-naphthalenedicarboxylic acid, and terephthalic acid.

5. A cosmetic composition as claimed in claim 4, wherein the non-sulfonated diacid monomer consists of about 50 to 90% by mole, of a lower dialkyl ester of one or more members selected from the group consisting of terephthalic acid, isophthalic acid, and 2,6-naphthalenedicarboxylic acid, said alkyl being methyl, ethyl, propyl, isopropyl, or butyl, and from about 10 to 50% by mole, of an acid, or anhydride thereof, of one or more members selected from the group consisting of isophthalic acid, 2,6-naphthalenedicarboxylic acid, and terephthalic acid.

6. A cosmetic composition as claimed in claim 5, wherein said non-sulfonated monomer consists of from about 70 to 90% by mole, a lower dialkyl ester of terephthalic acid, said alkyl being methyl, ethyl, propyl, isopropyl, or butyl and from about 10 to 30% by mole, of isophthalic acid or anhydride of isophthalic acid.

7. A cosmetic composition as claimed in claim 3, wherein the diol monomer is monoethylene glycol or diethylene glycol.

8. A cosmetic composition as claimed in claim 3, wherein the sulfonated diacid monomer is selected from the group consisting of sulfoisophthalic acid, sulfoisophthalic acid anhydride, methyl diester of sulfoisophthalic acid, sulfosuccinic acid, sulfosuccinic acid anhydride, and methyl diester of sulfosuccinic acid.

9. A cosmetic composition as claimed in claim 8, wherein the sulfonated diacid monomer is dimethyl sodio-5-oxysulfonylisophthalate.

10. A cosmetic composition as claimed in claim 3, wherein said sulfonated diacid monomer is used in an amount corresponding to a molar ratio: (sulfonated diacid monomer)/(non-sulfonated monomer)+(sulfonated diacid monomer) equals from about 5/100 to 40/100.

11. A cosmetic composition as claimed in claim 10, wherein said molar ratio is from about 10/100 to 15/100.

12. A cosmetic composition as claimed in claim 3, wherein in formula (I) W is an OH function or a group —A—Z, wherein:

A represents a divalent hydrocarbon group attached to the vicinal silicon atom via an Si—C or Si—O—C bond optionally containing a hetero atom selected from the group consisting of O, Si, N and S, and Z represents a group which can react with at least one of the above monomers under the polymerization conditions.

13. A cosmetic composition as claimed in claim 12, wherein W is selected from the group consisting of:

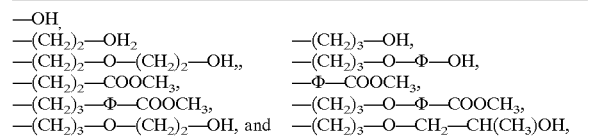

wherein Φ is phenyl.

14. A cosmetic composition as claimed in claim 1, comprising:

from about 0.1 to 5%, of its weight of said sulfonated copolyester containing polyorganosiloxane units, and from about 5 to 99.5%, of its weight of said vehicle.

15. A cosmetic composition as claimed in claim 1, in the form of a rinsing formula, a lotion, a shampoo, a conditioner for the hair, a mousse for styling, a mousse for combing, a gel for styling, a gel for combing the hair, a hand lotion, a body lotion, a cleansing milk, a make-up-removing composition, a product for regulating skin moisturization, a care cream, a cream for protecting against sunlight and ultraviolet radiation, a milk for protecting against sunlight and ultraviolet radiation, an anti-acne preparation, a local analgesic, a mascara, a toiletry bar or a soap.

16. A cosmetic composition as claimed in claim 1, wherein the vehicle is water, water containing a solvent to dissolve or disperse the copolymer, or water containing a solvent to dissolve or disperse the copolymer and volatile silicones.

17. A cosmetic composition as claimed in claim 16, wherein the vehicle is in the form of a water-in-oil emulsion, an oil-in-water emulsion, an oil-in-water-in-silicone emulsion, a mousse, an aerosol, or a spray.

18. A cosmetic composition as claimed in claim 16, wherein said composition further comprises one or more additives selected from the group consisting of fixing resins, cationic resins, polymer compounds exerting a protective function, plasticizers, surfactants, wetting agents, emollients, inorganic particles, preserving agents, viscosity-modifying polymers, dispersing agents, fragrances, dyes, and pigments.

* * * * *